United States Patent [19]

Child

[11] 4,281,658
[45] Aug. 4, 1981

[54] DILATOR

[75] Inventor: Francis W. Child, Eagle Bend, Minn.

[73] Assignee: Child Laboratories, Inc., Eagle Bend, Minn.

[21] Appl. No.: 55,994

[22] Filed: Jul. 9, 1979

[51] Int. Cl.³ .......................................... A61M 29/00
[52] U.S. Cl. .................................. 128/341; 128/274; 119/14.19; 222/112
[58] Field of Search ............... 128/341, 343, 348, 350, 128/349, 130, 274; 119/71, 14.19, 14.2, 14.21; 222/212, 494, 528; 251/342

[56] References Cited

U.S. PATENT DOCUMENTS

| | | | |
|---|---|---|---|
| 111,932 | 2/1871 | Hewitt | 119/14.19 |
| 393,161 | 11/1888 | Law | 119/14.21 |
| 1,045,326 | 11/1912 | Ruflin | 128/349 |
| 1,116,379 | 11/1914 | Browning | 119/14.22 |
| 1,242,314 | 10/1917 | Bean | 128/349 R |
| 1,688,795 | 10/1928 | Aas | 128/348 R |
| 1,995,051 | 3/1935 | Benson | 119/14.21 |
| 2,450,217 | 9/1948 | Alcorn | 128/350 |
| 2,687,731 | 8/1954 | Iarussi et al. | 128/349 |
| 2,704,076 | 3/1955 | Larson | 128/348 |
| 2,816,552 | 12/1957 | Hoffman | 128/305 |
| 2,827,054 | 3/1958 | Towne | 128/341 |
| 3,030,960 | 4/1962 | Turner et al. | 128/348 |
| 3,071,139 | 1/1963 | Nicholson | 128/350 |
| 3,308,808 | 3/1967 | Cohen | 128/766 |
| 3,703,898 | 11/1972 | Zackheim | 128/341 X |
| 3,768,102 | 10/1973 | Kwan-Gott et al. | 3/1 |
| 3,821,956 | 7/1974 | Gordhamer | 128/343 |
| 3,825,157 | 7/1974 | Herzig | 222/212 |
| 3,831,629 | 8/1974 | Mackal et al. | 137/525 |
| 3,881,448 | 5/1975 | Hallstrom | 119/14.19 |

OTHER PUBLICATIONS

Honda, Service Repair Handbook, All Civic Models, 1973-1974, Clymer Publications.
L. S. Goldman & A. Gilman, *The Pharmacological Basis Of Therapeutics*, Second Edition, MacMillan Co., 1955, NY, p. 1105.
J. H. Moyer III & G. M. Piersol, *The Cyclopedia Of Medicine, Surgery, Specialties*, vol. XII, F. A. Davis Co., Philadelphia, 1964, p. 693.
D. F. Williams & R. Roaf, *Implants in Surgery*, W. B. Saunders Co., Ltd., 1973, p. 9.

*Primary Examiner*—Stephen C. Pellegrino
*Attorney, Agent, or Firm*—Burd, Bartz & Gutenkauf

[57] ABSTRACT

A dilator for a test of a female mammal operates to facilitate the flow of fluids from the teat. The dilator has a body having a passage adapted to be positioned in communication with a duct of the teat. Elongated finger structure extends from the body into the duct. In one form of the dilator, the finger structure has a pair of angle shaped flexible fingers secured at one end to the body and at the opposite end to a sleeve. In another form, the finger structure is an elongated tubular member having a passage allowing the flow of fluid through the dilator. A one-way valve mounted on the body allows the flow of fluid out of the dilator and restricts the entrance of external foreign substances back into the passage and duct of the teat. The valve has flexible side walls terminating in normally closed lips. A slit mouth is located between the lips. The slit mouth can be opened to facilitate the dispensing of medicinal compounds into the teat and udder of the mammal.

59 Claims, 22 Drawing Figures

U.S. Patent Aug. 4, 1981 Sheet 1 of 3 4,281,658
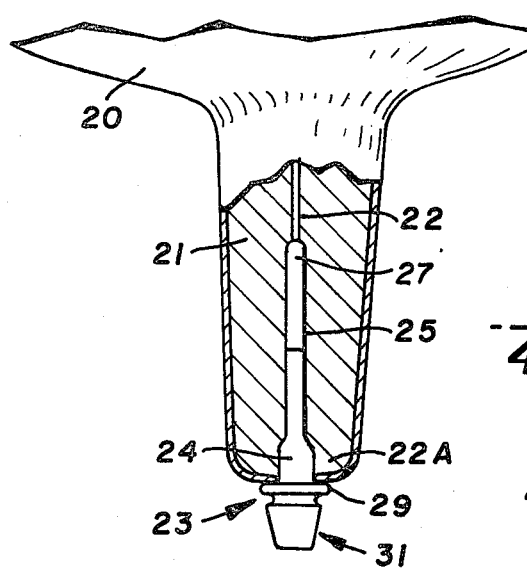
FIG. 1
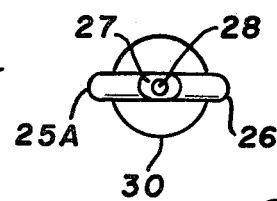
FIG. 4
FIG. 4A
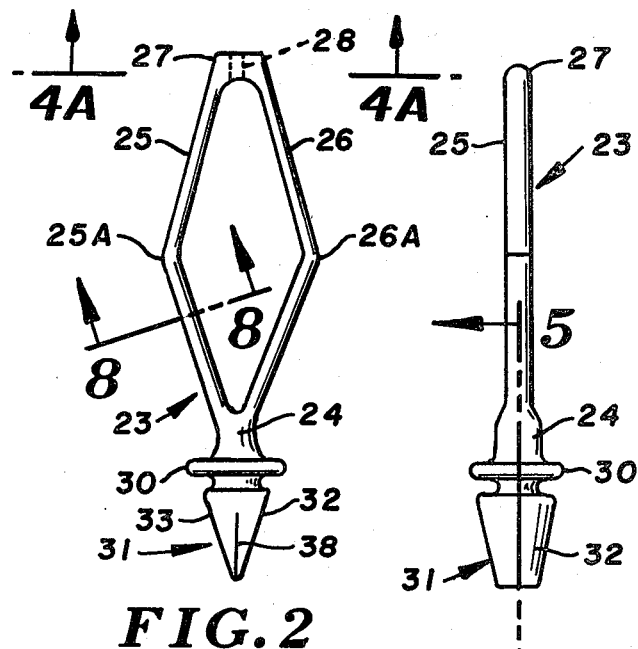
FIG. 2
FIG. 3
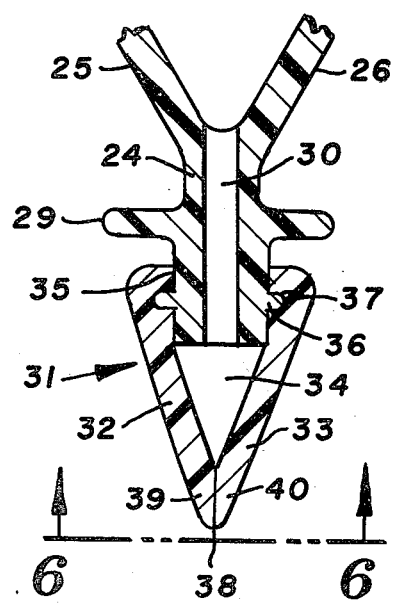
FIG. 5
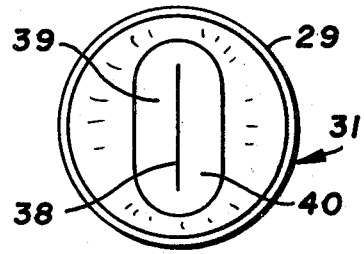
FIG. 6
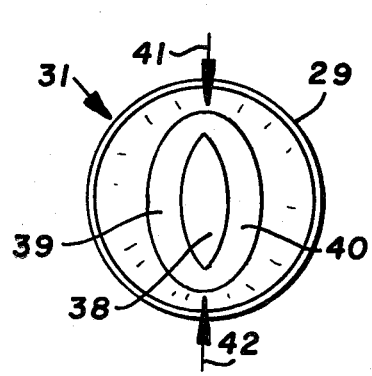
FIG. 7
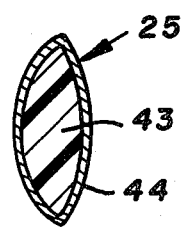
FIG. 8

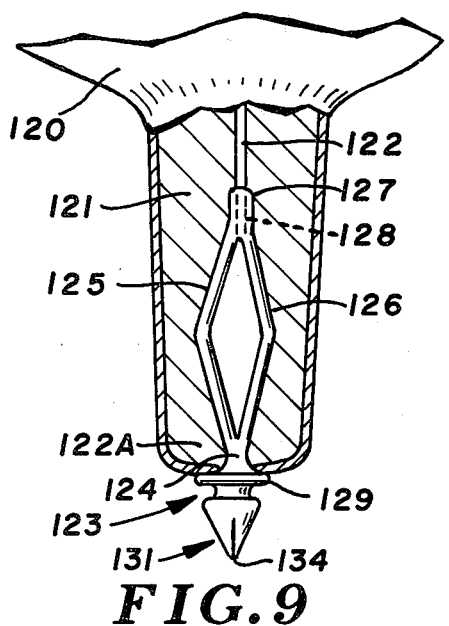
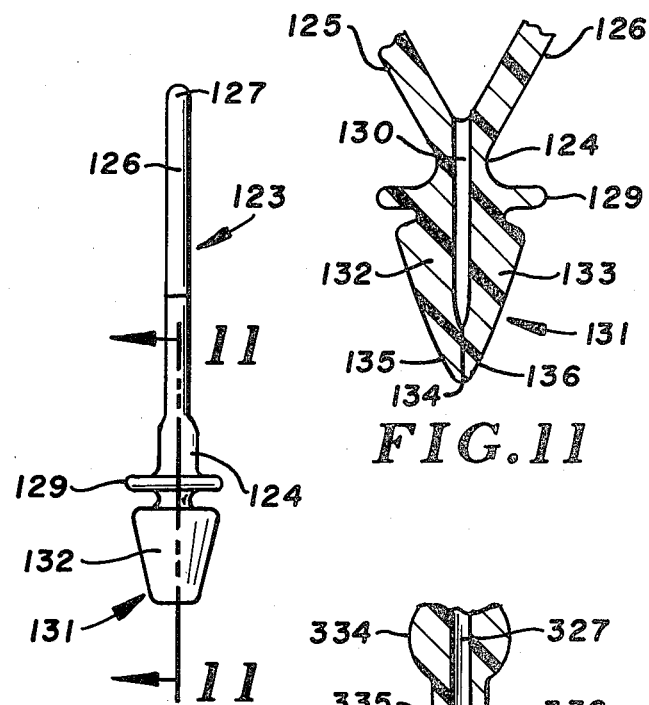
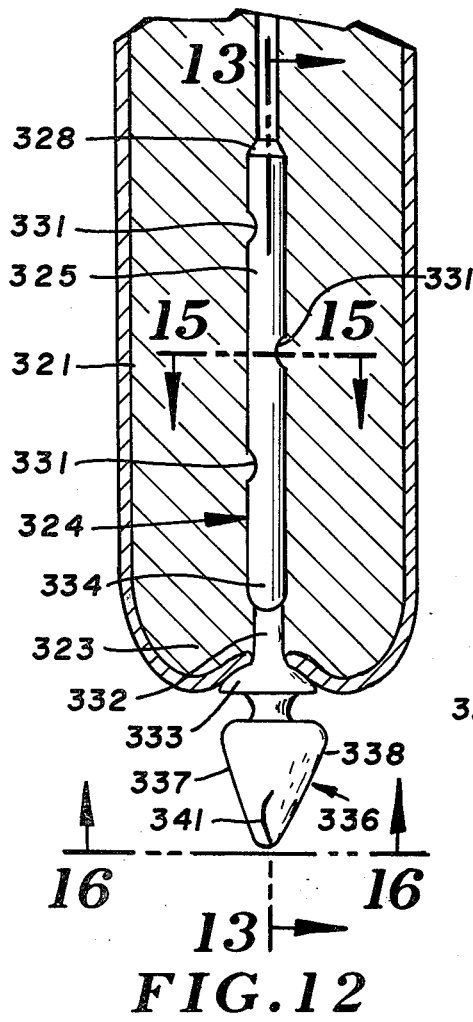
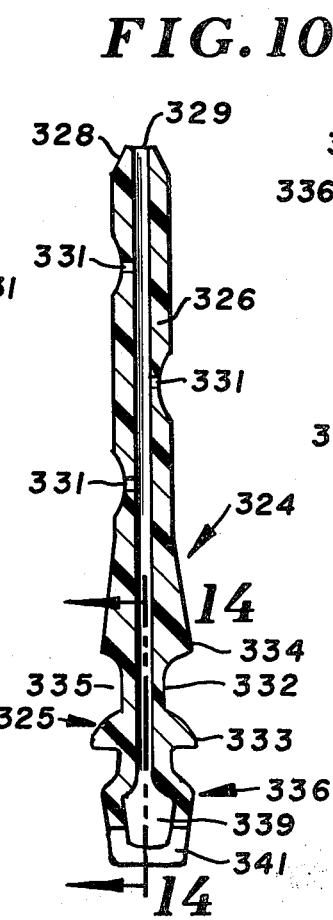
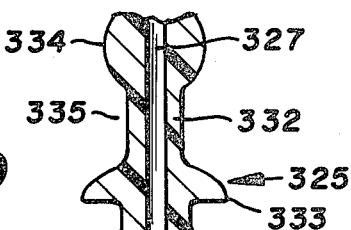
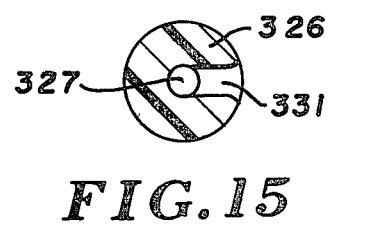
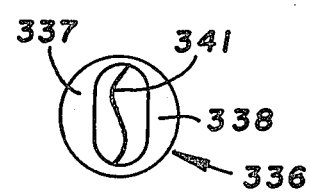
FIG. 9  FIG. 10  FIG. 11  FIG. 12  FIG. 13  FIG. 14  FIG. 15  FIG. 16

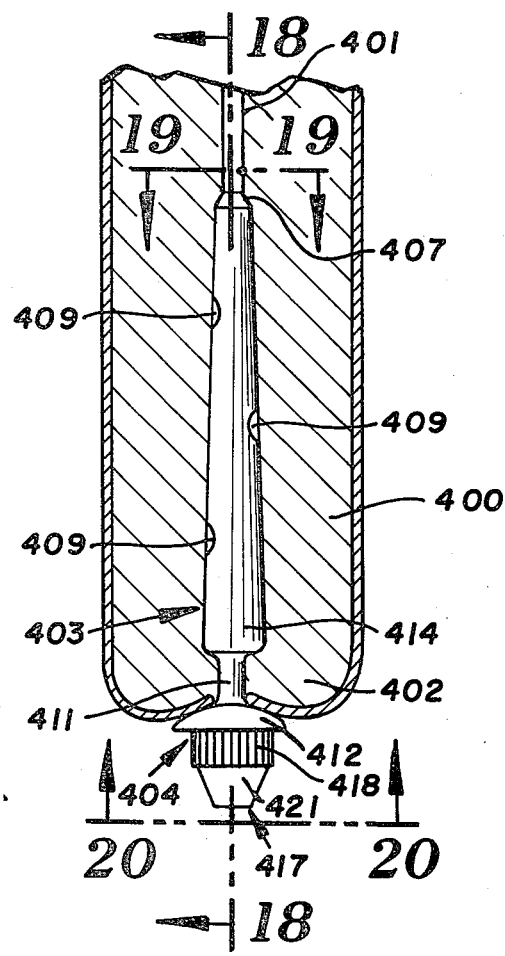
FIG. 17
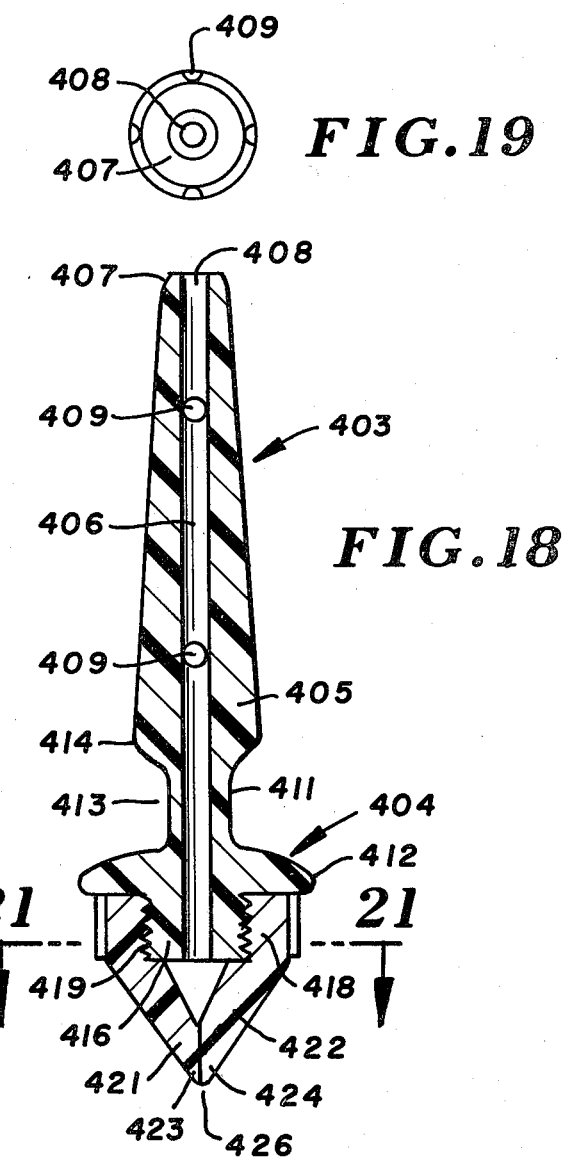
FIG. 19
FIG. 18
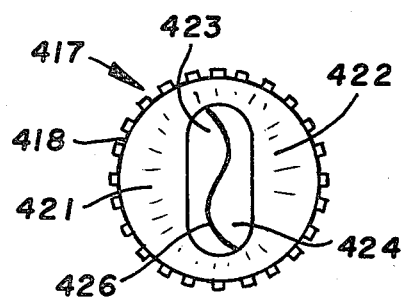
FIG. 20
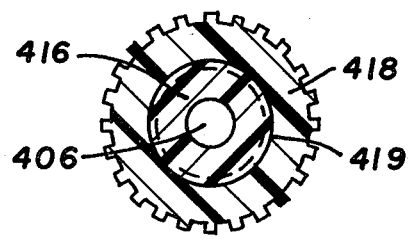
FIG. 21

4,281,658

DILATOR

SUMMARY OF INVENTION

The invention is related to an apparatus adapted to be inserted into a passage in a body, such as a body member or tissue, to facilitate the movement of fluid through the passage in one direction and restrict or limit the flow of fluid and external substances back into the passage. The apparatus has a first means having a passage for carrying fluid. The first means is adapted to be located in the body so that the fluid in the body can flow through the passage of the first means out of the body. A one-way valve means is associated with the first means to allow fluid to flow out of the passage of the first means and restrict the movement of material located externally of the body back into the passage of the valve means and thereby contaminate the body tissue.

More particularly, the apparatus is a dilator for use to control the flow of fluid, such as milk, from the teat of a bovine animal or a caprine animal. The dilator has a tubular body having a longitudinal passage. A finger structure is secured to the body and is extended along the longitudinal axis of the body. A portion of the body and finger structure is adapted to be inserted into the duct of the teat to facilitate the flow of fluid through the teat. A one-way valve means is mounted on the body. The one-way valve means operates to permit the flow of liquid through the dilator and the teat externally of the teat and restrict or prevent the entrance of foreign substances, both liquid and solid, bacteria, viruses, and the like from moving through the dilator and into the teat canal. The dilator body also is in firm engagement with the sphincter muscle of the teat to minimize the entrance of foreign substances around the dilator into the teat. The one-way valve means has flexible side walls that terminate in normally closed lips. A slit between the lips forms a slit mouth that is normally closed. The flexible side wall can be enlarged to open the mouth and thereby permit the free flow of fluid through the dilator. The valve means can be removably detached from the body. Preferably, the valve means is an integral part of the body.

The finger structure in one form of the dilator has a plurality of separate elongated flexible fingers. Each finger has a forward end joined to a sleeve. The sleeve has a passage to allow the fluid to flow to the body of the dilator. The fingers have first and second sections angularly disposed relative to each other to fill the teat cavity above the sphincter muscle of the teat. In another form of the invention the finger structure is an elongated tubular member having a longitudinal passage and a plurality of side holes open to the passage to facilitate the flow of fluid through the passage and into the passage.

The body and finger structure of the dilator can have an interior or core of structural material, such as plastic, metal, or the like, that is coated with a heavy metal, such as silver or gold. The alternate portions of the finger structure can be coated with silver and gold. The coating metals have ion activity that causes bactericidal ions of silver or gold to be released into the tissue proximate the finger structure.

IN THE DRAWINGS

FIG. 1 is an elevational view partly in section of a teat of a mammal with a dilator embodying the invention inserted in the milk duct of the teat;

FIG. 2 is a front elevational view of the dilator;

FIG. 3 is a side elevational view of the dilator of FIG. 2;

FIG. 4 is a top plan view of FIG. 2;

FIG. 4A is an enlarged sectional view taken along the line 4A—4A of FIG. 2;

FIG. 5 is an enlarged sectional view taken along line 5—5 of FIG. 3;

FIG. 6 is a view of the dilator one-way valve means taken along the line 6—6 looking in the direction of the arrows of FIG. 5;

FIG. 7 is a view similar to FIG. 6 showing the valve mouth in the open position;

FIG. 8 is an enlarged sectional view taken along the line 8—8 of FIG. 2;

FIG. 9 is an elevational view partly in section of a teat of a mammal with a first modification of the dilator of the invention inserted in the milk duct of the teat;

FIG. 10 is an enlarged side elevational view of the dilator of FIG. 9;

FIG. 11 is an enlarged sectional view taken along the line 11—11 of FIG. 10;

FIG. 12 is an elevational view of a second modification of the dilator of the invention in inserted relation with the teat of a mammal shown in section;

FIG. 13 is an enlarged sectional view taken along the line 13—13 of FIG. 12;

FIG. 14 is an enlarged sectional view taken along line 14—14 of FIG. 13;

FIG. 15 is an enlarged sectional view taken along the line 15—15 of FIG. 12;

FIG. 16 is an end view of the one-way valve unit of a dilator of FIG. 12 viewing along line 16—16 in the direction of the arrows;

FIG. 17 is a third modification of the dilator of the invention in inserted relation with the teat of a mammal shown in section;

FIG. 18 is an enlarged sectional view taken along the line 18—18 of FIG. 17;

FIG. 19 is a top view of the dilator shown in FIG. 17 viewing along line 19—19 in the direction of the arrows;

FIG. 20 is a bottom view of the valve unit dilator of FIG. 17 viewing along line 20—20 in the direction of the arrows; and FIG. 21 is an enlarged sectional view taken along the line 21—21 of FIG. 18.

DESCRIPTION OF PREFERRED EMBODIMENTS

Referring to FIG. 1, there is shown a portion of the mammary system of a mammal having an elongated teat 21. Teat 21 is an elongated muscular member extended from an udder 20 to a terminal end. A duct 22 extends longitudinally through teat 21 and terminates at the lower end thereof. A sphincter muscle 22A functions to close the outlet end of duct 22. The teat hereinafter described is a teat of a bovine animal, as a milk cow. The dilator of the invention can be used in teats of other mammals, as caprine animals. The dilator's use is not limited to use with teats of mammals. The dilator can be inserted into body and tissue ducts and cavities to control the flow of fluid in one direction from the ducts and cavities.

As shown in FIGS. 2, 3, and 4, dilator designated generally at 23 has a cylindrical body or tubular member 24 having a longitudinal passage 30. Body 24 has a continuous cylindrical wall surrounding passage 30. A plurality of flexible fingers 25 and 26 are integral with the upper end of body 24. Fingers 25 and 26 have forward ends secured to a sleeve 27. Sleeve 27, shown in FIGS. 2, 4, and 4A, is a short cylindrical member having a longitudinal passage 28 generally aligned with passage 30 in body 24. Each finger has first and second segments joined at a mid-section or knee 25A and 26A, respectively. The segments are angularly oriented relative to each other. The segments of each of the fingers 25 and 26 are generally equal in length and extend outwardly from the longitudinal axis of dilator 23. As shown in FIG. 2, in the relaxed position, the segments of each of the fingers 25 and 26 have an angle of approximately 135 degrees relative to each other. Other angular relationships between the first and second segments of each finger can be used. Alternatively, the fingers 25 and 26 can have an arcuate or convex configuration. The number of fingers can vary. For example, 3, 4, or 5 fingers can be secured to the end of body 24. Each finger has an outwardly directed configuration to retain the fingers in duct 22 of teat 21. Fingers 25 and 26 expand the teat chamber of duct 22 thereby facilitating the flow of fluid through duct 22 in response to compression or squeezing forces on teat 21.

The mid-section of body 24 has an outwardly directed annular flange or stop 29. As shown in FIG. 1, when fingers 25 and 26 and sleeve 27 are fully inserted in duct 22, flange 29 is in engagement with the lower or bottom end of teat 21. Flange 29 functions as a stop and indicator of the in or full inserted position of dilator 23. The sphincter muscle 22A surrounds a neck of body 24. The neck is located between the lower ends of fingers 25 and 26 and flange 29. The neck of body 24 has a generally cylindrical outer surface which is surrounded by the sphincter muscle 22A. This prevents foreign fluids and materials, bacteria, viruses, and the like from entering duct 22. The body 24, fingers 25 and 26, and sleeve 27 are a one-piece plastic unit made from suitable plastic, as polyethylene. Other types of plastics can be used to make the dilator.

A one-way valve designated generally at 31 is mounted on the lower end of the body 24. One-way valve 31 functions to allow fluid, as milk, to flow out of the teat duct 22 through passage 30 and restrict movement of liquid and solid material, bacteria, viruses, and the like back into the teat duct 22. As shown in FIG. 4, valve 31 has downwardly converging flexible side walls 32 and 33 enclosing a chamber 34. Side walls 32 and 33 have generally U-shaped configurations with tapering side surfaces and tapering ends converging to a generally flat end or nose. Chamber 34 is open to the discharge end of passage 30. The upper end of side wall 32 has a circular hole 35 accommodating and surrounding body 24. Body 24 has an outwardly directed annular rib 36 that fits into an inwardly open annular groove 37 in the upper end of side walls 32 and 33. The side walls 32 and 33 are of flexible plastic or rubber material. The upper end of the side walls is stretched and yieldably mounted on body 24. Rib 36 retains the valve unit on body 24. Valve 31 can be removed from body 24 by snapping the side walls 32 and 33 from rib 36.

The lower end of valve 31 has a normally closed slit mouth 38. The mouth 38 is an elongated transverse slit separating mouth lips 39 and 40. As shown in FIG. 4, lips 39 and 40 are normally in engagement with each other to close the mouth 38. The mouth 38 is opened by applying oppositely directed forces, as shown by arrows 41 and 42 in FIG. 7. Resilient lips 39 and 40 move away from each other, thereby opening mouth 38. As soon as the forces are released from the opposite sides of lips 39 and 40, the lips will close mouth 38.

Referring to FIG. 8, finger 25 has a generally ellipsoidal cross section with a resilient plastic core 43. Each of fingers 25 and 26 can have any suitable cross sectional shape which allows the fingers to be bent to side-by-side positions. Core 43 can be of any resilient material, including, but not limited to, plastic, rubber, and metal. The outer surface of core 43 is entirely covered with a skin or coating 44. The coating 44 is a metal, such as silver, gold, or separate portions of silver and gold. Other types of materials can be used to make dilator 23. The body 24, fingers 25 and 26, and sleeve 27 can be metal, including, but not limited to, stainless steel and metal coated with a layer of silver or gold or separate sections of silver and gold. The silver and gold are compatible with the body tissue and fluids and have anti-bacterial action. Ion discharge from silver and gold destroys bacteria that is in the area of these metals.

Referring to FIGS. 9 to 11, there is shown a first modification of the dilator indicated generally at 123 located in a duct 122 of a teat 121. Teat 121 extends from an udder 120.

Dilator 123 has a cylindrical body or tubular member 124 having a central longitudinal passage 130. A plurality of longitudinally extended flexible fingers 125 and 126 are integral with the one end of body 124. Fingers 125 and 126 have first and second sections that are angularly related relative to each other at an angle of about 135 degrees. Fingers 125 and 126 are integral with a sleeve 127 having a longitudinal passage 128.

The mid-section of body 124 has an outwardly directed annular radial flange 129 which serves as a stop indicating the inserted position of dilator 123. As shown in FIG. 9, flange 129 engages the lower end of teat 121 when fingers 125 and 126 are located in duct 122. Sphincter muscle 122A is located around the neck of body 124 between the lower ends of fingers 125 and 126 and flange 129.

A one-way valve indicated generally at 131 is integral with the lower end of body 124. One-way valve 131 functions to allow fluid, as milk, to flow out of the teat duct 122 through passage 130 and restrict movement of liquid and solid material, bacteria, viruses, and the like back into the teat duct 122. Valve unit 131 has downwardly converging flexible side walls 132 and 133. Side walls 132 and 133 have generally U-shaped configurations with tapering side surfaces and tapering ends converging to a generally flat end or nose. Passage 130 extends between side walls 132 and 133. The lower ends of side walls 132 and 133 have flexible lips 135 and 136 leading to a normally closed slit mouth 134. The lips 135 and 136 have flat surfaces that are normally in engagement with each other forming the mouth 134. The mouth 134 is a transverse slit. The slit can be linear, as shown in FIGS. 9 and 11, or have other shapes, as curved, V-shape, Z-shape, or the like. The entire dilator 123 is a one-piece plastic member. The plastic member can be coated with a coating or skin of metal, such as silver, gold, or a mixture of silver and gold. Dilator 123 has the same structure as dilator 23, except that one-way valve 131 is integral with body 124.

Referring to FIGS. 12 to 16, there is shown a second modification of the dilator of the invention indicated generally at 324. Dilator 324 is shown in FIG. 12 as inserted up into a milk duct 322 of a teat 321 of a mammal, as a milk cow. The lower end of teat 321 has muscular tissue or sphincter muscle 323 that normally closes the lower or outlet end of milk duct 322. Sphincter muscle 323 surrounds a neck portion of the dilator 324 to retain the dilator in an inserted position in the teat 321.

Dilator 324 has an elongated cylindrical member or body indicated generally at 325. A tubular finger or member 326 extends upwardly from body 325. A longitudinal passage 327 extends through finger 326 and body 325. Finger 326 terminates in a semi-spherical or rounded open forward end 328 to facilitate the insertion and movement of the finger 326 up into the milk passage 322. A passage 327 has an open or upper end 329 in communication with the upper end of milk duct 322. The sides of finger 326 have a plurality of holes 321 which provide access to the center portion or cavity of the teat 321 to insure the flow of milk from the teat into the passage 327.

Body 325 has a cylindrical neck 332 joined to an enlarged flange or head 333 and a curved outwardly directed shoulder 334 on an interior or adjacent end of finger 326. An annular groove 325 surrounds neck 322 to accommodate the sphincter muscle 323 when the dilator is properly inserted into milk duct 322 of teat 321.

A one-way valve indicated generally at 336 is secured to the lower or outer end of body 325. Valve 336, shown in FIG. 14, has a pair of downwardly converging side walls 337 and 338 that surround a chamber 339. Side walls 337 and 338 have generally U-shaped configurations with tapering side surfaces and tapering ends converging to a generally flat end or nose. Chamber 339 is in communication with passage 327 which extends through body 325. The lower end of valve unit 336 has a normally closed mouth 341 defined by a pair of flexible lips 342 and 343. The lips 342 and 343 have complementary engaging surfaces that form the sides of mouth 341. As shown in FIG. 16, the mouth has a generally S-curved shape which allows the mouth 341 to be opened in response to a pressure of the milk in passage 327. Mouth 341 can be a straight line or slit. Other shapes, such as a Z shape, can be used for the mouth 341. Lips 342 and 343 have an elastic strength and memory so that the mouth 341 is closed under the normal pressure of the milk and milk duct 322. When the pressure of the milk in the duct 322 exceeds the normal limit, such as during the milking of the mammal, the valve mouth 342 will open to allow the milk to flow through the dilator 324. With the mouth 341 normally closed, it prevents the entrance of foreign liquid and solid materials, bacteria, viruses, and the like from moving up passage 327 and contaminating the teat tissue and udder.

Body 325, finger 326, and valve unit 336 are of a one-piece construction. The entire dilator 324 can be made of a flexible plastic, as polyethylene. Finger 326 can be coated with a material, such as metal, including, but not limited to, silver or gold, or a mixture of silver and gold.

Referring to FIGS. 12 to 21, there is shown a fourth modification of the dilator of the invention indicated generally at 403 in inserted relationship in a milk duct 401 of a teat 400 of a mammal, as a milk cow. Teat 400 has a lower end 402, including the sphincter muscle which is located about a neck portion of dilator 403, to hold the dilator 403 in inserted position in the teat 400.

Dilator 403 has a cylindrical tubular body 404 joined to an upwardly directed tubular finger or member 405. Body 404 and finger 405 have a longitudinal passage 406 for carrying milk from the upper portion of milk duct 401 through the teat 400. The upper or forward end of finger 405 has a rounded or curved end 407 to facilitate the insertion of finger 405 into milk duct 401. End 407 has an opening 408 forming the open forward end of passage 406. The sides of finger 405 have a plurality of holes 408 providing passages into the longitudinal passage 406. The milk in the mid and lower portion of the teat 401 flows through the holes 409 into passage 406.

The body 404 has a cylindrical neck 411 joined to an outwardly directed annular flange 412. The upper end of neck 411 is joined to an enlarged shoulder 414 on the lower or interior end of finger 405. An annular groove or recess 413 surrounding neck 411 between flange 412 and shoulder 414 accommodates the portion of the sphincter muscle 402 in the lower end of teat 400. The upper or forward surface of flange 412 engages the lower end of teat 400 when the finger 405 is properly inserted in the milk duct 401. A cylindrical projection or boss 416 extends downwardly from flange 412. Passage 406 extends through boss 416. A one-way valve indicated generally at 417 is releasably mounted on boss 416. Valve 417 functions to allow fluid, as milk, to flow out of the teat duct 401 through passage 406 of member 405 and restrict movement of liquid and solid material, bacteria, viruses, and the like back into passage 406. Valve 417 minimizes contamination of the teat tissue with external substances. Valve 417 is a generally cup-shaped member having a sleeve 418. Sleeve 418 has threads which engage with complementary threads on boss 416 to hold the valve unit on the boss. Other types of releasable connecting means, such as the rib shown in FIG. 6, can be used to attach valve 417 to boss 416. Valve 417 and body 404 can be an integral one-piece member, made from plastic, metal, or the like.

One-way valve 417 has a pair of downwardly or outwardly converging flexible side walls 421 and 422. The lower engaging portions of side walls 421 and 422 have lips 423 and 424 which provide a normally closed mouth 426. Mouth 426 has engaging surfaces that close the exit to passage 406. The side walls 421 and 422 have generally U-shaped configurations with tapering side surfaces and tapering ends converging to a generally flat lower end or nose. As shown in FIG. 19, mouth 426 has a generally S-shaped slit along the lower end of the lips 423 and 424. Mouth 426 can be an elongated linear slit extended along lips 423 and 424. Other shapes, such as a Z-shaped slit, can be used for mouth 426.

In use, the valves 31, 131, 336, and 417 provide one-way valving for the out flow of fluid, as milk, through the body passages. The valve lips are normally in an engaging position to close the mouth. This prevents the movement of contaminants, as bacteria, up into the passage, teat duct, and udder. The means attached to the body as one or more fingers is inserted up into the milk duct through the discharge end of the duct. When the one or more fingers are properly inserted into the duct, the lower end of the teat engages the stop flange. The teat sphincter muscle surrounds the neck and is located in the annular channel around the neck. The sphincter muscle holds the dilator in the inserted position in the teat. The milk in the duct can flow down the duct into the passage. In dilators 324 and 403, the milk in the lower portion of the teat flows through the side holes 331 and 409 into the passage. The pressure of the milk in the passage due to a milking machine or hand milking is sufficient to open the valve lips and the lips away from each other thereby opening the mouth.

Dispensers having dispensing probes can be used to inject medicinal compounds into the teat and udder of the mammal. The valve lips, being flexible, allow the probe to be inserted up into the passage so that the material can be discharged into the passage.

While there has been shown and described the preferred embodiments of the dilator of the invention, it is understood that changes in the materials, structure, arrangement of structure, and size and length of the parts may be made by those skilled in the art without departing from the invention. The invention is defined in the following claims.

The embodiments of the invention in which an exclusive property or privilege is claimed are defined as follows:

1. A dilator for a teat of a female mammal, said teat having a longitudinal duct in communication with a duct outlet in the end of the teat comprising: body means having a passage adapted to be positioned in the duct outlet to allow fluid to flow through the end of the teat, means secured to said body means adapted to be inserted into the duct through the duct outlet in the end of the teat to facilitate flow of fluid in the duct to the passage of the body means, and one-way valve means mounted on said body means for allowing fluid to flow out of the duct through said passage of the body means and discharge the fluid externally of the teat, said valve means having at least a pair of flexible side walls, each side wall surrounding a valve chamber open to said passage of the body means, said side walls projecting from the body means and extended toward each other, said lips of the side walls having cooperating edges surrounding a normally closed slit mouth to restrict entrance of external foreign substances into the passage of the body means and the duct of said teat.

2. The dilator of claim 1 wherein: said means secured to said body means includes a plurality of separate elongated fingers.

3. The dilator of claim 1 wherein: said means secured to said body means includes a plurality of separate elongated fingers having forward ends and sleeve means joined to the forward ends of the fingers.

4. The dilator of claim 3 wherein: said fingers comprise a pair of fingers secured at one end to said body means and at the other end to said sleeve means.

5. The dilator of claim 3 wherein: each finger has first and second sections angularly disposed relative to each other.

6. The dilator of claim 3 wherein: each finger has a flexible core and a metal coating covering the core.

7. The dilator of claim 6 wherein: the metal coating is silver.

8. The dilator of claim 3 wherein: said sleeve means has a passage generally aligned with the passage in the body means.

9. The dilator of claim 1 including: means on said body means engageable with the end of the teat when the means secured to said body means is located in the duct.

10. The dilator of claim 9 wherein: said means on said body means is a radially outward directed flange.

11. The dilator of claim 1 including: means releasably connecting the side walls of the valve means to the body means.

12. The dilator of claim 1 wherein: said valve means has at least one elongated slit forming the mouth.

13. The dilator of claim 1 wherein: said valve means has flexible side walls integral with said body means.

14. The dilator of claim 13 wherein: said valve means has at least one elongated slit forming the mouth.

15. The dilator of claim 1 wherein: said means secured to said body means includes a pair of flexible fingers having forward ends, sleeve means joined to the forward ends of the fingers, said sleeve means having a passage generally aligned with the passage in the body means, each finger having first and second sections outwardly directed and angularly related to each other.

16. The dilator of claim 1 wherein: said one-way valve means and body means are a one-piece unit.

17. The dilator of claim 1 wherein: the body, means secured to the body means, and one-way valve means are a one-piece unit.

18. The dilator of claim 1 wherein: said one-way valve means has a normally closed linear slit mouth.

19. The dilator of claim 1 wherein: said means secured to the body means comprise an elongated tubular member.

20. The dilator of claim 19 wherein: said tubular member has a longitudinal passage and a plurality of openings open to said passage and the sides of the tubular member.

21. The dilator of claim 19 including: an outwardly annular flange secured to the body means.

22. The dilator of claim 1 wherein: said body means and one-way valve means have coacting means allowing the valve means to be removed from the body means.

23. The dilator of claim 22 wherein: said coacting means includes a flange and groove on the body means and valve means.

24. The dilator of claim 22 wherein: said coacting means includes a threaded connection between the body means and valve means.

25. The dilator of claim 1 wherein: said one-way valve means has a pair of flexible side walls, each of said side walls having a lip in contact with an adjacent lip to form a normally closed slit mouth.

26. The dilator of claim 1 including: an outwardly directed flange secured to said body means, said body means having an annular neck between said flange and the means secured to said body means for accommodating a part of the lower end of the teat.

27. A dilator for a teat of a female mammal, said teat having a duct in communication with the end of the teat comprising: a tubular body having a passage adapted to be located in communication with said duct, finger means secured to said body adapted to be inserted into said duct from the end of the teat, each of said finger means having first and second sections outwardly directed and angularly disposed relative to each other, said sections biasing said finger means in outward directions, and one-way valve means mounted on said body for controlling the flow of fluid through said passage, said one-way valve means having a mouth and flexible lip means holding the mouth closed to restrict the movement of material located externally of the teat into the passage and duct.

28. The dilator of claim 27 including: an annular outwardly directed flange on said body, adapted to engage the end of the teat when the finger means are inserted in the duct.

29. The dilator of claim 27 including: sleeve means secured to the finger means remote from said body, said sleeve means having a passage generally aligned with the passage in said body.

30. The dilator of claim 27 wherein: said finger means have flexible cores and a metal coating covering said cores.

31. The dilator of claim 30 wherein: said metal coating is silver.

32. The dilator of claim 27 wherein: said valve means and body have coacting means for releasably connecting said valve means to said body.

33. The dilator of claim 27 wherein: said lip means has an elongated slit forming said mouth.

34. The dilator of claim 27 wherein: said valve means and body are an integral one-piece structure.

35. A dilator for a teat of a female mammal, said teat having a longitudinal duct and a duct outlet in the end of a teat comprising: a tubular body having a longitudinal passage, said body being adapted to be positioned in the outlet duct to allow the flow of fluid through the longitudinal passage, an elongated tubular member secured to said body adapted to be located in said duct when the body is positioned in said duct outlet, said tubular member having a longitudinal passage in communication with the passage of the body allowing fluid to flow through the tubular member and body, and a plurality of openings open to the passage in the tubular member allowing fluid to flow through said openings from the duct into the longitudinal passage of the tubular member, and one-way valve means mounted on said body for allowing fluid to flow through said passage of the body and discharge the fluid externally of the teat, said valve means having a plurality of flexible side walls extended away from the body and surrounding a valve chamber open to the passage of the body, each of said side walls having flexible lip means having cooperating edges surrounding a normally closed slit mouth to restrict movement of material located externally of the teat into the duct.

36. The dilator of claim 35 including: means on said body engageable with the end of the teat when the body is located in said duct outlet and the tubular member is located in said duct.

37. The dilator of claim 36 wherein: said means on said body has a radially outwardly directed annular flange.

38. The dilator of claim 35 including: means releasably connecting the valve means to the body.

39. The dilator of claim 35 wherein: said valve means has at least one elongated slit forming the cooperating edges of said lip means.

40. The dilator of claim 35 wherein: said valve means has flexible side walls integral with said body.

41. The dilator of claim 40 wherein: said valve means has at least one elongated slit forming the cooperating edges of said lip means.

42. The dilator of claim 35 wherein: the body, tubular member and one-way valve means are a one-piece unit.

43. The dilator of claim 35 wherein: said body and one-way valve means have coacting means allowing the valve means to be removed from the body.

44. The dilator of claim 35 including: an outwardly directed annular shoulder on said body, said shoulder being located in said duct when the body is located in the duct outlet.

45. The dilator of claim 35 including: outwardly directed annular flange on said body engageable with the end of the teat when the body is located in the duct outlet, and an outwardly directed annular shoulder on said body spaced from the flange, said shoulder being located in said duct when the body is located in the duct outlet, said shoulder cooperating with said teat with the end of the teat to hold the body in the duct outlet.

46. A dilator for the teat of a female mammal, said teat having a longitudinal duct and a duct outlet in the end of the teat, and a sphincter muscle surrounding the duct outlet for contracting the duct outlet to a closed position comprising: a tubular body having a first end and second end and a longitudinal passage extended from the first end to the second end, said body adapted to be located in the duct outlet whereby the sphincter muscle holds the annular portion of the end of the teat in engagement with the body, an outwardly annular flange on said body engageable with the end of the teat when the body is located in the duct outlet, and outwardly directed annular shoulder on said body spaced from said flange, said shoulder being located in said duct generally adjacent said annular portion of the end of the teat when the body is located in the duct outlet, said shoulder cooperating with said annular portion of the end of the teat to hold the body in the duct outlet, an elongated tubular member secured to the first end of the body adapted to be located in said duct when the body is located in said duct outlet, said tubular member having a longitudinal passage in communication with the passage of the body allowing fluid to flow through the tubular member and body, a plurality of openings open to the passage of the tubular member allowing fluid to flow from the duct into the longitudinal passage of the tubular member, and one-way valve means secured to the second end of the body, said valve means having at least a pair of flexible side walls surrounding a valve chamber open to the passage of the body, said side walls projecting away from the second end of the body and directed generally toward each other, said side walls terminating in flexible lips having cooperating edges providing a normally closed slit mouth to restrict the entrance of external foreign substances into the duct of the teat.

47. The dilator of claim 46 including: means releasably connecting the one-way valve means to the second end of the body.

48. The dilator of claim 46 wherein: said valve means has at least one elongated slit forming the mouth.

49. The dilator of claim 48 wherein: said means includes gold means for providing a gold ion discharge having anti-bacterial action.

50. The dilator of claim 46 wherein: said valve means is integral with said body.

51. The dilator of claim 46 wherein: the body, the tubular member, and one-way valve means are a one-piece unit.

52. The dilator of claim 46 wherein: said body and one-way valve means have coacting means on the valve means to be moved from the body.

53. The dilator of claim 46 wherein: said one-way valve means has a pair of flexible side walls, said side walls converging toward each other away from the second end of the body and terminating in flexible lips, said lips having cooperating linear edges that provide a normally closed linear slit mouth.

54. A dilator for the teat of a female mammal, said teat having a longitudinal duct and a duct outlet in the end of the teat comprising: means adapted to be inserted through the duct opening into the duct of the teat for facilitating the flow of fluid out of the duct, said means including silver means for providing a silver ion discharge having anti-bacterial action in the teat, said means including a body having a passage adapted to be located in the duct opening, and means attached to the body adapted to be located in said duct, said silver means being associated with said body, and one-way valve means secured to said body for allowing fluid to flow through the passage of the body externally of the teat, said one-way valve means having at least a pair of flexible side walls surrounding a valve chamber open to said passage of the body, said side walls projecting from the body and extended toward each other, each of said side walls having a flexible lip, said lip of the side walls having cooperating edges surrounding a normally closed slit mouth to restrict entrance of movement of foreign substances into the duct of said teat.

55. The dilator of claim 54 wherein: said means has a core, skin means covering said core, said skin means including said silver means.

56. The dilator of claim 55 wherein: said skin means includes gold means for providing a gold ion discharge having anti-bacterial action in the teat.

57. The dilator of claim 54 wherein: said skin means has separate portions of the silver and gold.

58. The dilator of claim 54 wherein: said means includes separate portions of silver means and gold means for providing a silver ion discharge and a gold ion discharge having anti-bacterial action in the teat.

59. The dilator of claim 54 wherein: said means includes at least one finger adapted to be located in said duct of the teat, said finger including said silver means.

* * * * *

UNITED STATES PATENT AND TRADEMARK OFFICE
CERTIFICATE OF CORRECTION

PATENT NO. : 4,281,658
DATED : August 4, 1981
INVENTOR(S) : Francis W. Child

It is certified that error appears in the above-identified patent and that said Letters Patent are hereby corrected as shown below:

In line 1 of the Abstract, "test" should be -- teat --.

Column 10, line 59, "on" should be -- allowing --.

Column 10, line 60, "moved" should be -- remove --.

Signed and Sealed this

Twenty-seventh Day of October 1981

[SEAL]

Attest:

GERALD J. MOSSINGHOFF

Attesting Officer     Commissioner of Patents and Trademarks